United States Patent
Cuevas et al.

(10) Patent No.: US 7,343,791 B2
(45) Date of Patent: Mar. 18, 2008

(54) SUTURE TESTER

(75) Inventors: Brian J. Cuevas, Middletown, CT (US); Frank R. Schiretz, Middletown, CT (US); Michael Prescott, Hamden, CT (US); Matthew Cohen, Berlin, CT (US); Robert DeSantis, Redding, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 583 days.

(21) Appl. No.: 11/075,613

(22) Filed: Mar. 9, 2005

(65) Prior Publication Data

US 2005/0234511 A1    Oct. 20, 2005

Related U.S. Application Data

(60) Provisional application No. 60/562,644, filed on Apr. 15, 2004.

(51) Int. Cl.
*G01L 5/04* (2006.01)
(52) U.S. Cl. ...................................................... 73/160
(58) Field of Classification Search ................. 73/159, 73/160
See application file for complete search history.

(56) References Cited

U.S. PATENT DOCUMENTS

| 1,436,323 | A | * | 11/1922 | Schnable et al. | ................. | 73/7 |
| 2,018,971 | A | * | 10/1935 | Paume | ............................. | 73/7 |
| 2,910,863 | A | * | 11/1959 | Hornbostel et al. | ............ | 73/86 |
| 3,209,589 | A | * | 10/1965 | Schlatter | ....................... | 73/160 |
| 3,726,137 | A | * | 4/1973 | Denton | ......................... | 73/160 |
| 3,831,444 | A | * | 8/1974 | Sasaki et al. | ................. | 73/160 |
| 3,942,532 | A | | 3/1976 | Hunter et al. | | |
| 4,116,393 | A | * | 9/1978 | Inouye et al. | ............... | 242/899 |
| 5,487,308 | A | * | 1/1996 | Demarest et al. | ............. | 73/827 |
| 5,584,858 | A | | 12/1996 | Totakura | | |
| 6,613,254 | B1 | * | 9/2003 | Shiffer | ........................ | 264/40.1 |
| 6,644,093 | B2 | * | 11/2003 | Roby et al. | ...................... | 73/7 |
| 2002/0173740 | A1 | | 11/2002 | Roby et al. | | |

OTHER PUBLICATIONS

Hong T. et al., Development of In Vitro Performance Tests and Evaluation of Nonabsorbable Monofilament Sutures for Cardiovascular Surgery, ASAIO Journal, vol. 44, No. 6, Nov. 1998.
European Search Report.

* cited by examiner

*Primary Examiner*—Hezron Williams
*Assistant Examiner*—John Fitzgerald

(57) ABSTRACT

A suture tester for evaluating fray resistance of surgical sutures. The suture tester comprises a reciprocating drive member, first, second, third and fourth pulleys, and a tensioning element. The pulleys each have a suture contact surface, which define a single plane. The third pulley is rotatable about this single plane. The first, second and third pulleys are all movable on the single plane. A suture is mounted in the suture tester such that one end is attached to the reciprocating drive member, it then passes to the first pulley, to the third pulley, to the second pulley and to the fourth pulley, before attaching to the tensioning element at the other end of the suture. The third pulley is then rotated and locked into place to form the desired number of suture wraps. The suture tester is started and causes the suture to rub against itself until it fails.

23 Claims, 5 Drawing Sheets

SUTURE TESTER

CROSS REFERENCE TO RELATED APPLICATIONS

The present application claims the benefit of priority from U.S. Provisional Patent Application Ser. No. 60/562,644, filed on Apr. 15, 2004. The disclosure of which is hereby incorporated by reference in its entirety.

BACKGROUND

1. Technical Field

The present disclosure generally relates to a fray tester for sutures. In particular, the disclosure relates to a test apparatus and related methods for evaluating surface durability in terms of fray resistance or breakdown performance of a suture when rubbing against itself or against a solid surface material.

2. Background of the Related Art

Sutures are often used in surgical procedures for holding cut tissue surfaces in apposition for a period of time sufficient for healing. Non-absorbable sutures, e.g. sutures made from non-bioabsorbable materials such as polyolefins, nylon, cotton and the like, are generally removed after a period of time or may remain as long term implants. Absorbable sutures, e.g. those fabricated from bioabsorbable materials such as polymers of lactide and glycolide, collagen, and the like, are gradually degraded and absorbed by the body, and do not require subsequent removal.

A suture having a good degree of flexibility and pliability can conform closely to body tissue without undue pressure. Good flexibility and pliability enhance the degree to which a suture can be tied down, knotted and securely placed in a desired position. Various attempts have been made to modify and optimize the physical characteristics of gut sutures. For example, various suture coatings and tubing fluids have been developed to achieve or enhance flexibility and pliability, and also to improve the handling characteristics of sutures, such as fray resistance or run-down performance.

In addition to the research efforts on suture materials, coatings and tubing fluids, several testing techniques have been adopted for evaluating such handling characteristics of sutures.

An example of a fray resistance test is described in U.S. Pat. No. 5,584,858. Such fray tester utilizes a static suture wound around rollers, and a dynamic suture wrapped twice at a point around the static suture with a weight attached at one end of the dynamic suture, the dynamic suture being subject to rubbing cycle against the static suture until the sutures break to stop the test.

SUMMARY

The present disclosure is directed to a suture tester for evaluating fray resistance characteristics of surgical sutures. Simulating real surgical operations where the surgeon repeatedly knots the suture, the suture tester is adapted to provide repeated rubbing action at a wrapped portion of the suture while counting the number of such rubbing cycles until the suture fails. Since the suture also comes into contact with human tissue and synthetic material while serving as a short and long term implantable device, the suture tester of this invention can also be adapted to simulate those conditions with repeated rubbing action between the suture and a solid surface material.

The suture tester comprises first, second and third pulleys with first, second and third suture contact surfaces respectively, a tensioning element, and a reciprocating drive member. In operation, a suture having a first end and a second end is mounted to the reciprocating drive member at its first end, passes from the first pulley, to the third pulley, to the second pulley, and is subject to the tensioning element at its second end. The first, second and third suture contacting surfaces define a single plane, which the third pulley can be rotated about to form the desired number of suture wraps.

In a preferred embodiment, the location of the first and second pulleys is adjustable, as they can be moved along the x-axis for changing the angle of incidence the suture creates. The third pulley can also be adjustable, as it can be moved along the y-axis, for changing the angle of incidence the suture creates.

The suture tester may further include a fourth pulley, with a fourth suture contact surface in the plane defined by the first, second and third suture contact surfaces. The suture passes to the fourth pulley after it passes the second pulley and before being subject to the tensioning element.

In a preferred embodiment, one or more of the suture contacting surfaces may be interchanged with another material. In this embodiment, the suture contacting surface(s) remains stationary as the suture passes it, for providing a means for testing the fray resistance of a suture when it is rubbed against a solid material. In this embodiment, it is not necessary to wrap the suture around itself.

In a preferred embodiment, the reciprocating drive member is a rotating wheel connected to a motor for providing reciprocating linear movement to the suture to be tested. The suture tester may further include a revolution counter for counting and displaying the number of cycles at the time the suture fails. Further, an automatic stop feature senses when the suture fails and consequently stops the reciprocating drive member.

In a preferred embodiment, the first end of a gripper arm is connected to the reciprocating drive member, and a suture gripper is attached to the second end of the gripper arm. The suture to be tested is held in place by the suture gripper. The suture gripper may travel along a slide for restricting the motion of the suture gripper to the x-axis.

BRIEF DESCRIPTION OF THE DRAWINGS

Preferred embodiments of the disclosure are described herein with reference to the drawings, wherein.

DETAILED DESCRIPTION OF PREFERRED EMBODIMENTS

Figure 1:
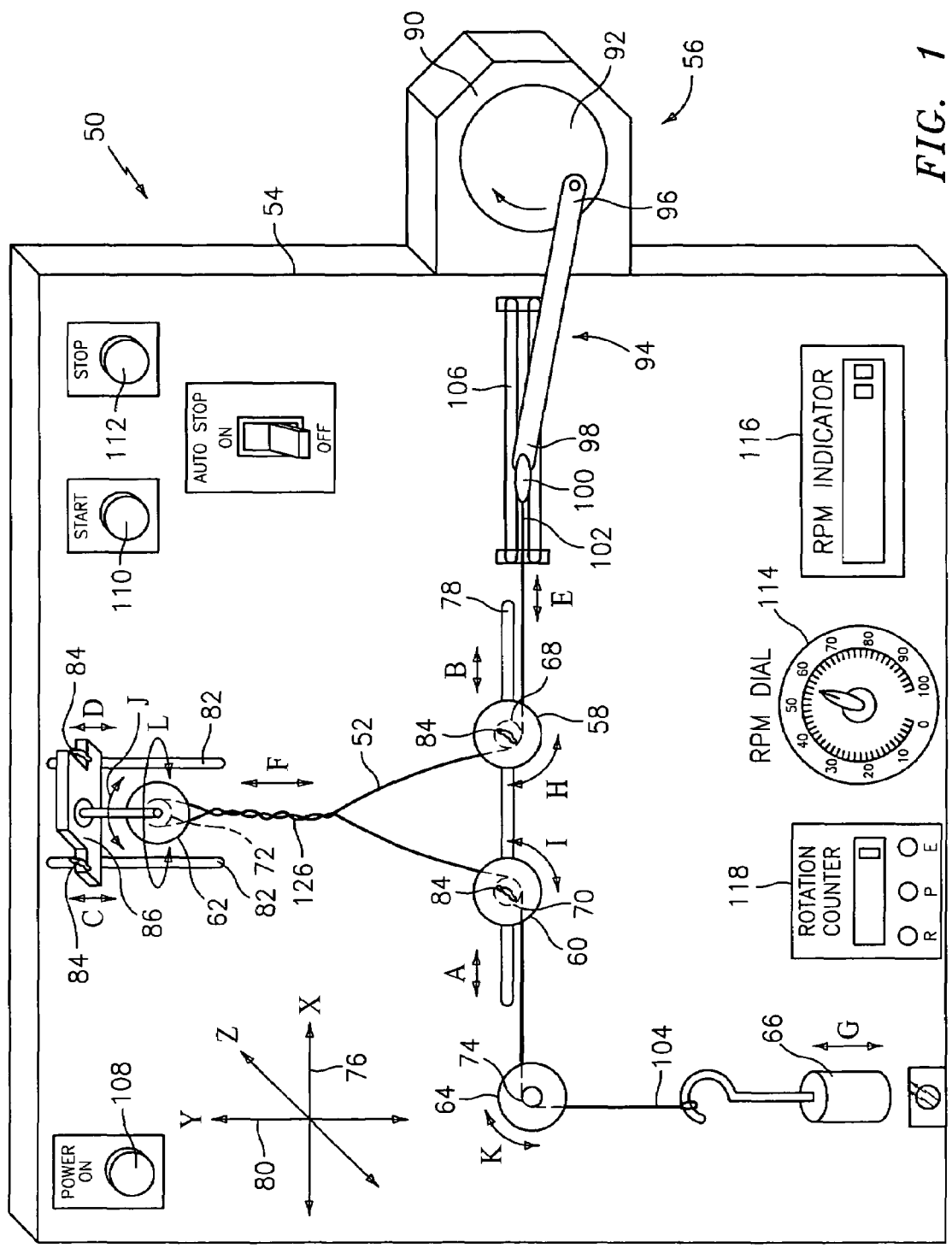
FIG. 1 is a front elevational view of a suture tester of the invention.

Referring now to the drawings in detail, FIG. 1 illustrates a suture tester, generally referred to by reference numeral 50, for measuring and evaluating fray resistance properties of a surgical suture 52 installed thereon as described hereinafter.

Suture tester 50 includes a frame 54, a reciprocating drive member 56, first, second, third and fourth pulleys 58, 50, 62 and 64 mounted on the frame 54, and a tensioning element 66 to apply appropriate tension to the suture 52 during the fray resistance test. The first, second, third and fourth pulleys 58, 60, 62 and 64 include first, second, third and fourth suture contact surfaces 68, 70, 72 and 74, respectively, for contacting the suture 52, and each pulley includes a suitable bearing (not shown) for providing free revolution to the pulleys in either direction. In a preferred embodiment, the first and second pulleys 58 and 60 can be moved along the x-axis 76 in a first track 78, and the third pulley can be moved along the y-axis 80 in a second track 82. A fastening device 84, such as a bolt, can pass through the first and second pulleys 58 and 60 and into the first track 78. The loosening and tightening of these bolts enables the first and second pulleys 58 and 60 to be moved along the x-axis 76 to their desired location, as indicated by double headed arrows A and B.

Figure 2:
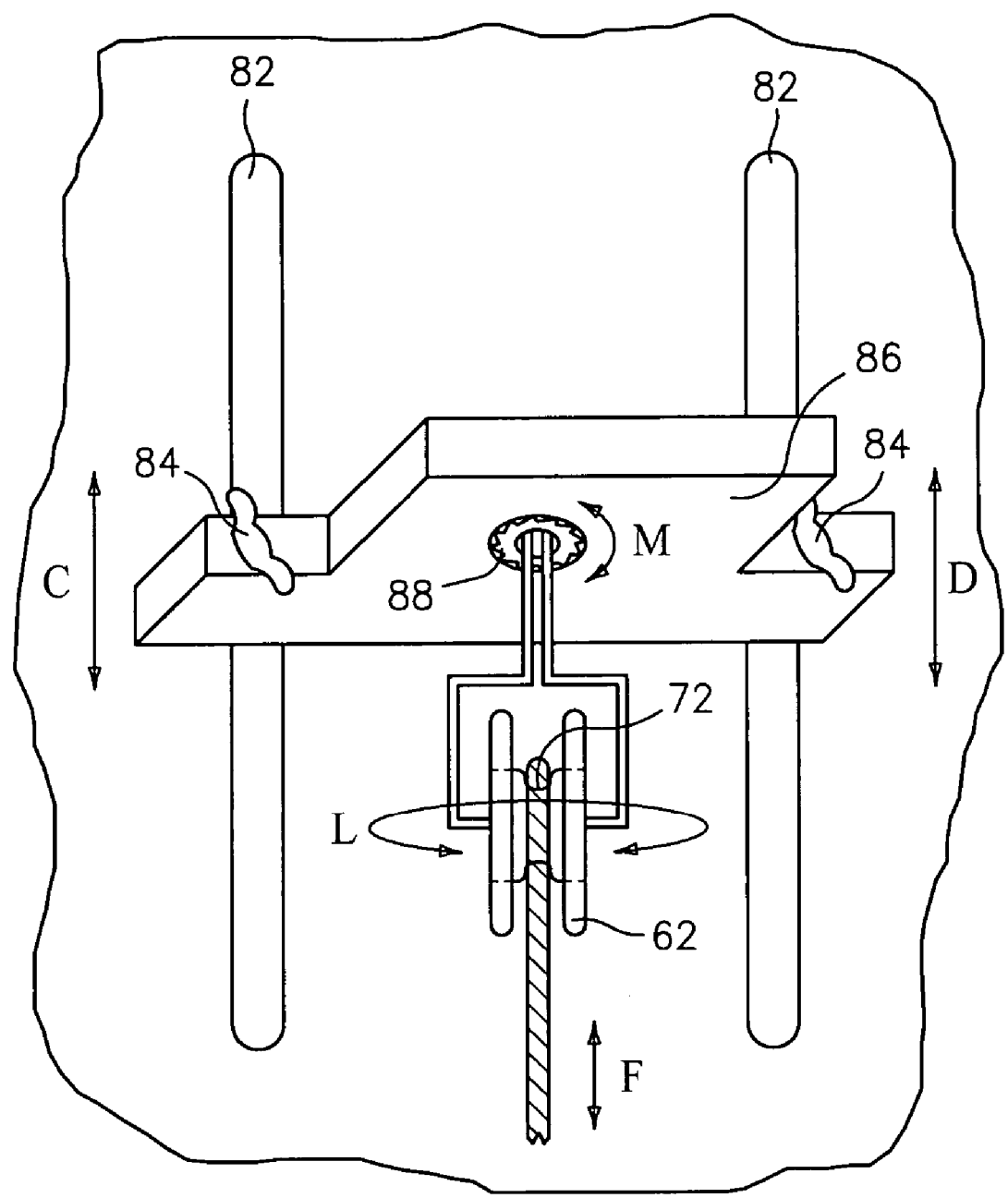
FIG. 2 is a perspective view illustrating the third pulley and the third suture contacting surface.

Now referring to FIG. 2, the third pulley 62 is suspended from a platform 86 for allowing the pulley 62 to rotate with respect to the plane defined by the first, second, third and fourth suture contact surfaces 68, 70, 72 and 74. This rotational movement is represented by arrows L and M. A locking device 88 is present adjacent the third pulley 62 for locking the pulley 62 into place after it has been rotated to prevent the pulley 62 from unwinding when the suture 52 passing it is subject to reciprocating motion. A fastening device 84 can pass through both sides of the platform 86, allowing for the third pulley's location on the y-axis 80 to be adjusted, as indicated by double headed arrows C and D. This enables the distance between each pulley and the angles the suture creates to be varied by the user of the suture tester. Other types of fastening devices and tracks for enabling the pulleys to be adjustable may be contemplated by the person ordinarily skilled in the art without substantially differing from the concept and principles of the present invention.

Referring now to FIG. 1, reciprocating drive member 56 preferably includes a motor 90 positioned on the frame 54, a rotating wheel 92, and a gripper arm 94 with a first end 96 and a second end 98. Gripper arm 94 is attached at its first end 96 to the rotating wheel 92 and at its second end 98 to a suture gripper 100 for holding the first end 102 of the suture 52. Preferably, the suture gripper 100 is freely rotatable relative to the gripper arm 94 in order to maintain the pointing direction of the suture 52 substantially toward the first pulley 58. The gripper arm's second end 98 is positioned on a slide 106 to restrict the motion of the suture gripper 100 to the x-axis 76, as indicated by doubled headed arrow E. Other types of reciprocating drive members for moving the suture relative to itself, including conventional driving mechanisms and suture gripping mechanisms, may be contemplated by the person ordinarily skilled in the art without substantially differing from the concept and principles of the present invention.

The suture tester 50 further includes a power switch 108, a start button 110 and a stop button 112 for starting and stopping the reciprocating motion of the reciprocating drive member 56, an RPM setting knob 114 for presetting the rotation speed of the rotating wheel 92, and RPM indicator 116 for displaying such rotation speed, and a rotation counter 118 for counting actual rotations of the rotating wheel 92 in real time. The suture tester 50 also includes a fail detector 120, which is described in detail below.

Referring to FIGS. 1 and 2, installation of the suture 52 for the suture test according to a preferable embodiment is described. A suture 52 to be tested is cut to an appropriate length. A first end of the suture 102 is then mounted to the suture gripper 100 of the suture tester 50. The suture 52 is then placed around the first pulley 58 and brought up vertically making, for example, about an 80 degree wrap around the pulley. Then, the suture 52 is guided over the third pulley 62, making about a 300 degree wrap around the pulley. The suture 52 is then guided to the second pulley 60 and then brought over horizontally, making about an 80 degree wrap around the second pulley. Then, the suture 52 is guided over the fourth pulley 64 and brought down vertically, making about a 270 degree wrap around the fourth pulley. Each of these angles created by the suture 52 is determined by the user of the suture tester 50 and can be substantially varied by repositioning the first, second and/or third pulleys 58, 60 and 62 by the means described above. A tensioning element 66 is hung at the second end of the suture 104 using an adequate loop portion made thereof, to provide an adequate tension to the suture 52 for the test. Next, the third pulley 62 is rotated to create the desired number of suture wraps and the pulley 62 is then locked into place. The tensioning element 66 is preferably a fifty (50) gram weight for conventional size 5/0 sutures. The actual weight of the tensioning element, the number of wraps of the suture, and the angles formed with the suture when it is wrapped around the first, second, third and fourth pulleys may differ depending on the suture materials, the size of the suture, and/or the adopted testing procedure.

Figure 4:
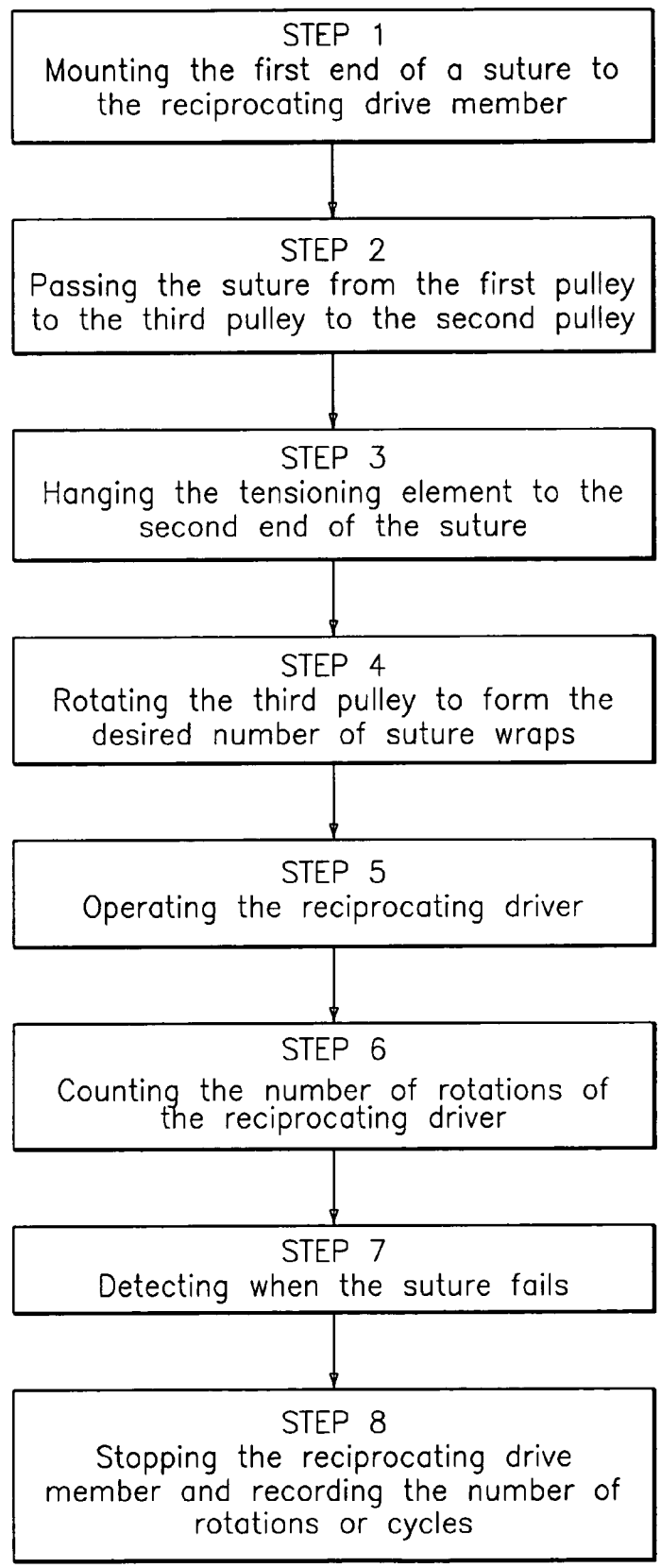
FIG. 4 is a flow chart illustrating major steps of the testing procedure of the invention.

Steps 1 to 4 in FIG. 4 summarize the major steps of the installation process described above.

Figure 5:
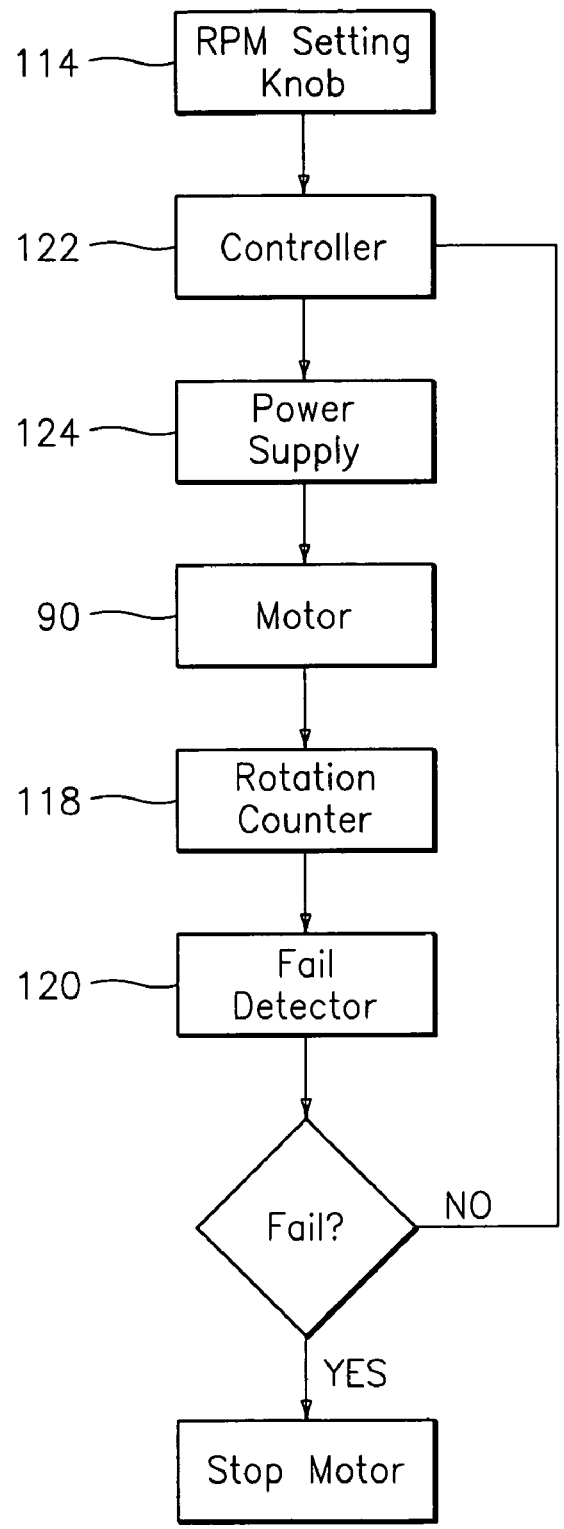

With respect to FIGS. 1 and 5, operation of the test procedure is described.

After installing the suture 52 to the suture tester 50 as described above, the power switch 108 is set to the on-position, the proper RPM is set using the RPM setting knob 114, and the rotation counter 118 is reset to zero. The range of RPM is preferably between 10 and 15, but may be adjusted accordingly per test procedure.

By pushing the start button 110, the suture tester begins its testing operation. A suitable controller 122 controls operation of motor 90 through power supply 124 and of other components of the tester. Rotation counter 118 is connected to motor 90 and counts the rotation of the motor in real time. As shown in FIG. 1, rotation of motor 90 provides reciprocating action to the suture's first end 102. This reciprocating action causes the suture's wrapped portion 126, and the tensioning element 66 to move substantially up and down as indicated by the doubled headed arrows F and G. In order to facilitate the reciprocating movement of the suture 52, the first, second, third and fourth pulleys 58, 60, 62 and 64 are subject to subordinate rotational movement to back and forth directions as indicated by arrows H, I, J and K. Thus, rotation of the motor 90 makes the suture 52 rub against itself at its wrapped portion 126 while suitable tension is applied to the suture by the tensioning element 66.

Upon repeated rubbing action, the suture's wrapped portion 126 becomes fragile and fails. Fail detector 120 is provided to detect such failure of the suture 52 and sends the corresponding signal to the controller 122 to stop running the motor 90. For detecting such failure of the suture 52, various detecting or sensing means (not shown) can be utilized. For example, a tension detector of known type may be disposed adjacent the suture gripper for detecting the change in tension occurring at the suture when it breaks, seizes or reaches the point that the tension exceeds a predetermined amount because of progress of fray in the suture. Another technique is to provide a sensor that can sense when a pulley has stopped, i.e. a failure has occurred and automatically triggers the motor to stop. Alternatively, a torque detector may be connected to the motor to detect the change in torque when the above-mentioned occurrence happens. It is also contemplated to add camera mounts and/or actual cameras to record the testing. This feature allows the operator to better quantify the failures.

Consequently, upon stopping of the motor 90, rotation counter 118 displays the number of actual rotations of the motor 90 or the rotating wheel 92 (i.e., the number of rubbing cycles) at the time the suture 52 fails.

Figure 3:
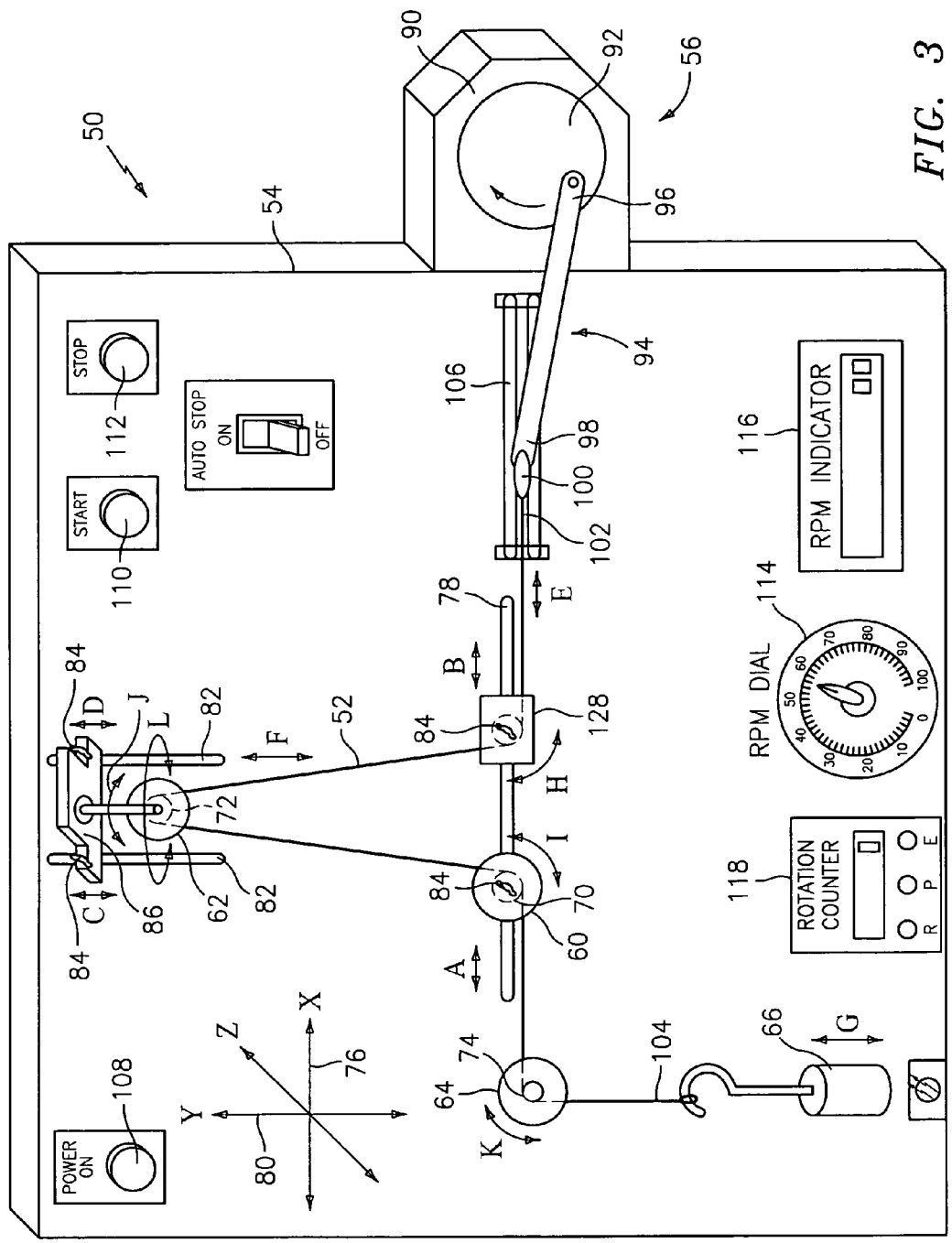
FIG. 3 is a schematic block diagram of one embodiment of the control system associated with the suture tester.

This process can also be followed to perform solid surface testing. To conduct a solid surface test, one or more of the suture contacting surfaces is replaced by a desired type of solid surface material 128, as shown in FIG. 3. In this embodiment of the invention, the solid surface material is not rotatable, and no suture wraps are necessary (i.e., the third pulley is not rotated). The suture is subject to the solid surface material as it moves back and forth and consequently rubs against the material until it ultimately fails or until the user stops the test. It is also contemplated by this invention to conduct both a typical test (suture on suture) and a solid surface test simultaneously by replacing one or more of the suture contacting surfaces with a solid surface material and by rotating the third pulley to create a desired number of suture wraps.

In addition to the suture installation process, steps 5 to 8 in FIG. 4 summarize the major steps of the testing process described above.

While the above description contains many specifics, these specifics should not be construed as limitations on the scope of the disclosure, but merely as exemplifications of preferred embodiments thereof. For example, in the preferred embodiment, there is a fourth pulley envisioned in a position substantially horizontal to the first and second pulleys, as shown in FIG. 1. However, the fourth pulley may be disposed in any relation to the first and second pulley, or the fourth pulley may be totally omitted from the suture tester all together. Those skilled in the art will envision many other possible variations that are within the scope and spirit of the disclosure as defined by the claims appended hereto.

What is claimed is:

1. A suture tester, comprising:
    a reciprocating drive member;
    a first pulley having a first suture contact surface;
    a second pulley having a second suture contact surface;
    a third pulley having a third suture contact surface, the first, second and third suture contact surfaces substantially defining a single plane;
    the third pulley being rotatable about the single plane; and
    a tensioning element,
    whereby a suture to be tested is operatively attached at one end to the reciprocating drive member, passes from the first pulley, to the third pulley, to the second pulley and is operatively attached to the tensioning element at the second end of the suture, whereby after suture attachment, the third pulley is rotated about the single plane to achieve a desired number of suture wraps.

2. The suture tester of claim 1 further including a fourth pulley in the single plane, whereby a suture passes to the fourth pulley after it passes to the second pulley and before it operatively attaches to the tensioning element.

3. The suture tester of claim 1, wherein one or more of the first, second or third suture contact surfaces can be interchanged with any sold material to allow for suture testing against a solid material.

4. The suture tester of claim 1 further including a speed control for setting the speed of the reciprocating drive member.

5. The suture tester of claim 1 further including a counter for counting the number of cycles of the reciprocating movement until a suture mounted in the suture tester fails.

6. The suture tester of claim 1 further including an automatic stop, for stopping the reciprocating drive member when a suture mounted in the suture tester fails.

7. The suture tester of claim 1 further including a locking device for locking the third pulley into place relative to the single plane defined by the first, second and third suture contacting surfaces.

8. The suture tester of claim 1, wherein the position of the first and second pulleys is adjustable.

9. The suture tester of claim 8, wherein the first and second pulleys are adjustable substantially about the x-axis.

10. The suture tester of claim 1, wherein the position of the third pulley is adjustable.

11. The suture tester of claim 10, wherein the third pulley is adjustable substantially about the y-axis.

12. The suture tester of claim 1, wherein the reciprocating drive member is rotatably adapted.

13. The suture tester of claim 12, wherein the reciprocating drive member includes a rotating wheel for providing reciprocating movement of a suture.

14. The suture tester of claim 13 further including a suture gripper operatively mounted to the rotating wheel.

15. The suture tester of claim 14 further including a slide for the suture gripper to travel along.

16. A method of testing fray resistance of a suture, comprising the steps of:
    providing a suture tester including a first pulley having a first suture contact surface, a second pulley having a second suture contact surface, a third pulley having a third suture contact surface, the first, second and third suture contacting surfaces substantially defining a single plane, the third pulley being rotatable about the single plane, a reciprocating drive member, and a tensioning element;
    providing a suture including a first end and a second end;
    mounting the first end of the suture adjacent the reciprocating drive member;
    passing the suture from the first pulley, to the third pulley, and to the second pulley;
    hanging the tensioning element adjacent the second end of the suture;
    rotating the third pulley about the single plane defined by the first, second and third suture contacting surfaces to achieve the desired number of suture wraps; and
    operating the reciprocating drive member and thereby providing reciprocating motion to the suture.

17. The method of testing fray resistance of a suture of claim 16 further including the step of passing the suture to a fourth pulley with a fourth suture contact surface after the suture passes from the second pulley and before hanging the tensioning element adjacent the second end of the suture.

18. The method of testing fray resistance of a suture of claim 16 further including the step of locking the third pulley into place relative to the single plane defined by the first, second and third suture contacting surface after rotating the third pulley about the single plane and before operating the reciprocating drive member.

19. The method of testing fray resistance of a suture of claim 16 further including the step of adjusting the location of one or more of the first, second or third pulleys for obtaining the desired angles of incidence.

20. The method of testing fray resistance of a suture of claim 16 further including the step of counting the number of rotations of the reciprocating drive member.

21. The method of testing fray resistance of a suture of claim 20 further including the step of recording the number of rotations of the reciprocating drive member.

22. The method of testing fray resistance of a suture of claim 16 further including the step of detecting when the suture fails.

23. The method of testing fray resistance of a suture of claim 22 further including the step of stopping the reciprocating drive member when the suture fails.

* * * * *